(12) United States Patent
Dyballa et al.

(10) Patent No.: US 9,862,738 B2
(45) Date of Patent: Jan. 9, 2018

(54) HETEROCYCLIC SELENOPHOSPHITES AND METHOD FOR THE PREPARATION THEREOF

(71) Applicant: EVONIK DEGUSSA GMBH, Essen (DE)

(72) Inventors: Katrin Marie Dyballa, Recklinghausen (DE); Robert Franke, Marl (DE); Detlef Selent, Rostock (DE); Armin Börner, Rostock (DE); Claudia Weilbeer, Bernburg (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/370,395

(22) Filed: Dec. 6, 2016

(65) Prior Publication Data

US 2017/0158722 A1  Jun. 8, 2017

(30) Foreign Application Priority Data

Dec. 7, 2015 (EP) .................................... 15198143

(51) Int. Cl.
  *C07F 9/655* (2006.01)
  *C07C 391/02* (2006.01)
  *C07F 9/6574* (2006.01)

(52) U.S. Cl.
  CPC ........ *C07F 9/65527* (2013.01); *C07C 391/02* (2013.01); *C07F 9/65744* (2013.01)

(58) Field of Classification Search
  None
  See application file for complete search history.

(56) References Cited

U.S. PATENT DOCUMENTS

| 2015/0336865 | A1 | 11/2015 | Dyballa et al. |
| 2015/0336885 | A1 | 11/2015 | Dyballa et al. |
| 2015/0336995 | A1 | 11/2015 | Dyballa et al. |

FOREIGN PATENT DOCUMENTS

| EP | 2949646 A1 | 12/2015 |
| WO | 2015181018 A1 | 12/2015 |
| WO | 2016139245 A1 | 9/2016 |

OTHER PUBLICATIONS

Chemical Abstract Registry No. 859821-79-7, indexed in the Registry File on STN CAS Online Aug. 12, 2005.*
International Search Report for EP 15 19 8143 dated May 20, 2016, 1 page.
Li, J. L. et al. Synthesis of phosphorus- and selenium-containing macrocycles and their complexation with Pd (II) $Cl_2$. Journal of the Chemical Society, Perkin Transactions 1, 2001, 1140-1146.
Franke, R., Selent, D., and Börner, A. Applied Hydroformylation. American Chemical Society, ACS Publications, Chemical Reviews, 2012. 5675-5732.

* cited by examiner

*Primary Examiner* — Alicia L Otton
*Assistant Examiner* — Po-Chih Chen
(74) *Attorney, Agent, or Firm* — Smith, Gambrell & Russell, LLP

(57) ABSTRACT

Novel heterocyclic selenophosphites, method for preparation thereof and use thereof as ligand unit for preparing ligands for use in complexes.

17 Claims, 1 Drawing Sheet

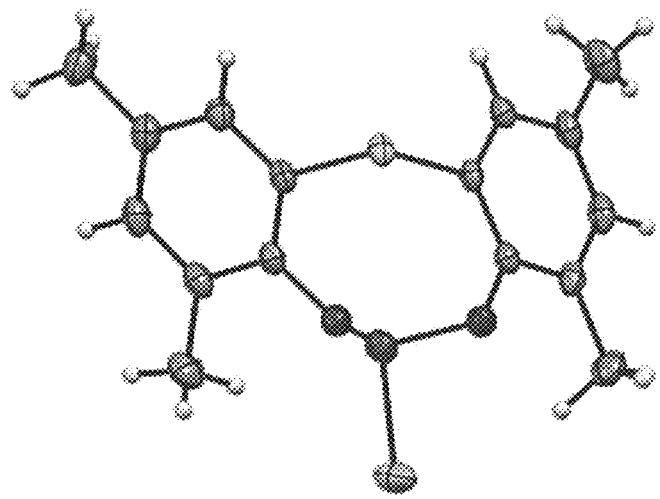

HETEROCYCLIC SELENOPHOSPHITES AND METHOD FOR THE PREPARATION THEREOF

Novel heterocyclic selenophosphites, method for preparation thereof and use thereof as ligand unit for preparing ligands for use in complexes.

The preparation of selenodiphenols unprotected on the hydroxyl group with low yields is known from T. K. Paine et al., "Manganese complexes of mixed O, X, O-donor ligands (X=S or Se): synthesis, characterization and catalytic reactivity", Dalton Trans., 2003, 15, 3136-3144). T. K. Paine et al. describes a synthesis of 2,2'-selenobis(4,6-di-tert-butylphenol) using selenium dioxide. The preparation of 2,2'-selenobis(4,6-di-tert-butylphenol) is effected here in an acidic medium with addition of concentrated hydrochloric acid. The product is obtained with a yield of only 25%.

H. M. Lin et al., "A novel and efficient synthesis of selenides", ARKIVOC, 2012, viii, 146-156, discloses another multi-stage synthetic route using Grignard reagents. A synthetic route to selenobiaryl ethers is disclosed in which bromine must be added to the corresponding phenol in order to then convert the product to a Grignard reagent with magnesium. The Grignard reagent can then react with the added selenium before the actual coupling to give the biaryl ether:

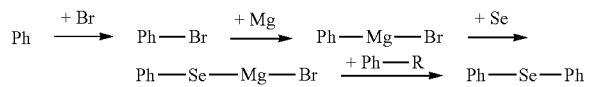

The product was obtained in a good yield, but this synthetic route is very complex, which makes it unattractive for industrial scale use. In this case, a multitude of synthetic steps are needed, the procedure for which is not uncritical in some cases, especially considering scale-up and using standards which are customary in industry. Moreover, this synthetic route gives rise to large amounts of waste products and solvents which have to be disposed of in a costly and inconvenient manner, one reason for which is the use of bromine.

EP 15168645.8 or U.S. Ser. No. 14/720,063 describes a large-scale economic synthetic route for preparing selenodiphenols.

The reactions between olefin compounds, carbon monoxide and hydrogen in the presence of a catalyst to give the aldehydes comprising one additional carbon atom are known as hydroformylation or oxo synthesis. In these reactions, compounds of the transition metals of group VIII of the Periodic Table of the Elements are frequently employed as catalysts. Known ligands are, for example, compounds from the classes of the phosphines, phosphites and phosphonites, each with trivalent phosphorus $P^{III}$. A good overview of the status of hydroformylation of olefins is found in R. Franke. D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

Rhodium-monophosphite complexes in catalytically active compositions are suitable for the hydroformylation of branched olefins having internal double bonds. Since the 1970s, there have been descriptions of the use of "bulky phosphites" in hydroformylation (see, inter alia, van Leeuwen et al., Journal of Catalysis, 2013, 298, 198-205). These feature good activity, but the nil selectivity for terminally oxidized compounds is low and in need of improvement.

In these hydroformylations, monophosphites and biphosphites are generally used, which are often formed from biphenol units. The development of novel ligands is frequently limited by the available biphenol, that is, ligand units. For instance, 2,2'-selenobiaryl ethers and also diphenylselenoxides and diphenylselenides represent a highly interesting class of compound. The 2,2'-selenobiaryl ethers are currently only being used in certain complexes, especially those containing manganese, but they have great potential for further uses.

The object of the invention was to provide a further wholly novel substance class of ligands and ligand units in order to broaden the field of available ligands for the respective specific complexes in catalysis. The object also consisted of producing ligands for rhodium hydroformylation catalysts. The object therefore also consisted of novel intermediates as ligand units for preparing ligands.

The objects are achieved with the heterocyclic selenophosphites according to Claim 1, the method according to Claim 6 and the use according to Claim 12. Particular embodiments are disclosed in the dependent claims and also detailed in the description. The objects are achieved preferably with selenophosphites of structures I, Ia, Ib, Ic and Id. Here, the hydroxy- or chloro-functional selenophosphites of structure I, Ia, Ib, Ic and Id are particularly preferred intermediates as ligand units for preparing ligands such as phosphite ligands.

BRIEF DESCRIPTION OF THE DRAWINGS

Further features and advantages of the invention can be ascertained from the following detailed description that is provided in connection with the drawings described below:

FIG. 1 shows a ball-and-stick model of compound 2c.

The invention provides at least one compound of a heterocyclic selenophosphite of the general structure I

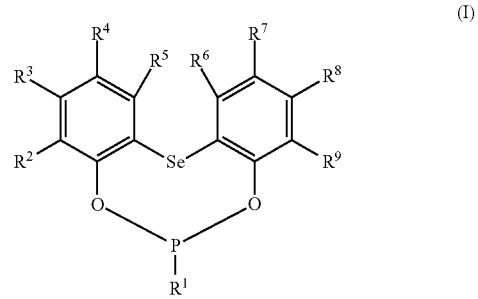

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3$H, —CN, —N[($C_1$-$C_{12}$)-alkyl]$_2$, wherein the alkyl and aryl groups may each independently be unsubstituted or substituted, wherein the respective substituted —($C_1$-$C_{12}$)-alkyl group and substituted —($C_6$-$C_{20}$)-aryl group, particularly comprising the alkyl and/or aryl groups in —($C_1$-$C_{12}$)-alkyl, —O—($C_1$-$C_{12}$)-alkyl, —($C_6$-$C_{20}$)-aryl, —O—($C_6$-$C_{20}$)-aryl, —OC=O—($C_1$-$C_{12}$)-alkyl, may have at least one substituent and the at least one substituent is each independently selected from —($C_3$-$C_{12}$)-cycloalkyl, —($C_3$-$C_{12}$)-heterocycloalkyl,
—($C_6$-$C_{20}$-aryl, fluorine, chlorine, cyano, formyl, acyl or alkoxycarbonyl, and
where —$R^1$ is independently selected from —OH and -Hal, and -Hal is selected from fluorine, chlorine, bromine, iodine, particularly preferably chlorine and bromine, particularly preferably chlorine, wherein optionally the compound I is present in a mixture with a rearrangement product of structure I. The invention also provides a composition comprising at least one compound of structure I, in particular comprising a compound of structure Ia optionally in a mixture with the rearrangement product according to structure Ia* or a compound of structure Ib.

According to an embodiment variant, the compound of the heterocyclic selenophosphite of the general structure I can be present as a compound of structure Ia in a mixture with a compound of structure Ia*,

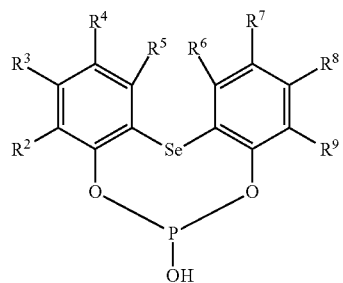

(Ia)

where $R^2$, $R^3$, $R^4$, $R^5$, $R^6$, $R^7$, $R^8$ and $R^9$ in structure Ia are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3$H, —CN, —N[($C_1$-$C_{12}$)-alkyl]$_2$, wherein the alkyl and aryl groups may each be independently unsubstituted or substituted, wherein the respective substituted —($C_1$-$C_{12}$)-alkyl group and substituted —($C_6$-$C_{20}$)-aryl group may have at least one substituent and the at least one substituent may each be independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl,

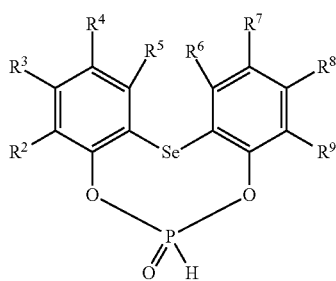

(Ia*)

and where $R^2$, $R^3$, $R^4$, $R^5$, $R^6$, $R^7$, $R^8$ and $R^9$ in structure Ia* may each be independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3$H, —CN, —N[($C_1$-$C_{12}$)-alkyl]$_2$, wherein the alkyl and aryl groups may each be independently unsubstituted or substituted, wherein the respective substituted —($C_1$-$C_{12}$)-alkyl group and substituted —($C_6$-$C_{20}$)-aryl group may have at least one substituent and the at least one substituent may each be independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl.

According to a further particularly preferred alternative, the heterocyclic selenophosphite of the general structure I is present as a compound of structure Ib.

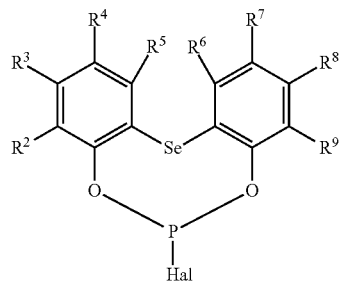

(Ib)

where $R^2$, $R^3$, $R^4$, $R^5$, $R^6$, $R^7$, $R^8$, and $R^9$ in structure Ib may each be independently selected from: —H, —($C_1$-$C_{12}$)-alkyl, —O—($C_1$-$C_{12}$)-alkyl. —($C_6$-$C_{20}$)-aryl,
—O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3$H, —CN, —N[($C_1$-$C_{12}$)-alkyl]$_2$, wherein the alkyl and aryl groups may each be independently unsubstituted or substituted, wherein the respective substituted —($C_1$-$C_{12}$)-alkyl group and substituted —($C_6$-$C_{20}$)-aryl group may have at least one substituent and the at least one substituent may each be independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl and where -Hal is independently selected from fluorine, chlorine, bromine, iodine, particularly preferably chlorine and bromine, particularly preferably chlorine.

Furthermore, it may be preferable if the heterocyclic selenophosphite of the general structure I is selected from at least one compound of structure Ic and Ic*, wherein optionally the compounds of structures Ic and Ic* may be present as a mixture.

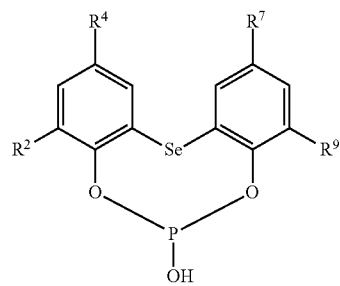

(Ic)

-continued

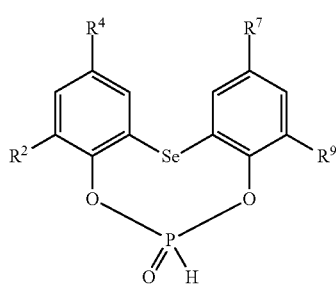
(Ic*)

where $R^2$, $R^4$, $R^7$, and $R^9$ in structures Ic and Ic* may each be independently selected from: —$(C_1$-$C_{12})$-alkyl, —O—$(C_1$-$C_{12})$-alkyl, —$(C_1$-$C_{20})$-aryl, —O—$(C_6$-$C_{20})$-aryl, -halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, wherein the alkyl and aryl groups may each be independently unsubstituted or substituted, wherein the respective substituted —$(C_1$-$C_{12})$-alkyl group and substituted —$(C_1$-$C_{20})$-aryl group may have at least one substituent and the at least one substituent may each be independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl. By way of preference, $R^2$, $R^4$, $R^7$, and $R^9$ in structures Ic and Ic* may each be independently selected from: —$(C_1$-$C_{12})$-alkyl, —O—$(C_1$-$C_{12})$-alkyl, particularly preferably $R^2$, $R^4$, $R^7$ and $R^9$ being methyl. Alternatively, $R^2$, $R^4$, $R^7$ and $R^9$ may be selected from methyl, ethyl, propyl, tert-butyl, methoxy and isopentyl.

According to a further alternative, the heterocyclic selenophosphite of the general structure I may be selected from at least one compound of structure Id,

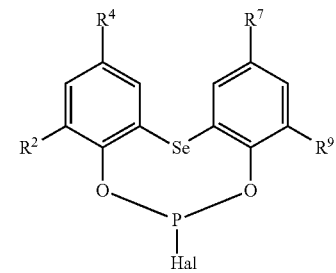
(Id)

where $R^2$, $R^4$, $R^7$ and $R^9$ in structure Id may each be independently selected from: —$(C_1$-$C_{12})$-alkyl, —O—$(C_1$-$C_{12})$-alkyl, —$(C_6$-$C_{20})$-aryl, —O—$(C_1$-$C_{20})$-aryl, -halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, wherein the alkyl and aryl groups may each be independently unsubstituted or substituted, wherein the respective substituted —$(C_1$-$C_{12})$-alkyl group and substituted —$(C_1$-$C_{20})$-aryl group may have at least one substituent and the at least one substituent may each be independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, where -Hal in structure Id is selected from fluorine, chlorine, bromine, iodine, preferably chlorine or bromine, particularly preferably chlorine. By way of preference, $R^2$, $R^4$, $R^7$ and $R^9$ in structure Id may each be independently selected from: —$(C_1$-$C_{12})$-alkyl, —O—$(C_1$-$C_{12})$-alkyl, particularly preferably $R^2$, $R^4$, $R^7$ and $R^9$ being methyl. Alternatively, $R^2$, $R^4$, $R^7$ and $R^9$ may be selected from methyl, ethyl, propyl, tert-butyl, methoxy and isopentyl.

The invention also provides the aforementioned structures of the selenophosphites and selenodiaryls of structures I, Ia, Ia* and Ib with $R^2$, $R^3$, $R^4$, $R^5$, $R^6$, $R^7$, $R^8$ and $R^9$ each being independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, wherein the alkyl and aryl groups are each independently unsubstituted.

The invention also provides the aforementioned structures of the selenophosphites and selenodiaryls of structures Ic, Ic* and Id with $R^2$, $R^4$, $R^7$ and $R^9$ each being independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, wherein the alkyl and aryl groups are each independently unsubstituted.

In an alternative. $R^2$. $R^3$, $R^4$, $R^5$, $R^6$, $R^7$, $R^8$ and $R^9$ in a heterocyclic selenophosphite of the general structure I, Ia, Ia* and Ib are each independently selected from: —H and —$(C_1$-$C_{12})$-alkyl and/or —O—$(C_1$-$C_{12})$-alkyl groups, wherein the alkyl groups may be linear, branched or cyclic.

In an alternative, $R^2$, $R^4$, $R^7$ and $R^9$ in a heterocyclic selenophosphite of the general structure Ic, Ic* and Id are each independently selected from:

—H and —$(C_1$-$C_{12})$-alkyl and/or —O—$(C_1$-$C_{12})$-alkyl groups, wherein the alkyl groups may be linear, branched or cyclic.

According to a particularly preferred embodiment variant, $R^2$, $R^3$, $R^4$, $R^5$, $R^6$, $R^7$, $R^8$ and $R^9$ in the selenophosphites of structures I, Ia, Ia* and Ib are each independently selected from: —H, unsubstituted —$(C_1$-$C_{12})$-alkyl and/or unsubstituted —O—$(C_1$-$C_{12})$-alkyl groups, wherein the alkyl groups may be linear, branched or cyclic.

According to a particularly preferred embodiment variant, $R^2$, $R^4$, $R^7$, $R^9$, in the selenophosphites of structures Ic, Ic* and Id are each independently selected from: —H, unsubstituted —$(C_1$-$C_{12})$-alkyl and/or unsubstituted —O—$(C_1$-$C_{12})$-alkyl groups, wherein the alkyl groups may be linear, branched or cyclic.

Further preferred selenophosphites comprise structures I:
(i) where $R^2$, $R^3$, $R^4$, $R^5$, $R^6$, $R^7$, $R^8$, $R^9$ are each independently selected from: —H, —$(C_1$-$C_{12})$-alkyl, —O—$(C_1$-$C_{12})$-alkyl,
(ii) where $R^2$, $R^3$, $R^4$, $R^5$, $R^6$, $R^7$, $R^8$, $R^9$ are each independently selected from: —H and —$(C_1$-$C_{12})$-alkyl or —H and —O—$(C_1$-$C_{12})$-alkyl,
(iii) where $R^2$, $R^4$, $R^7$, $R^9$ are each independently selected from: —$(C_1$-$C_{12}$-alkyl, —O—$(C_1$-$C_{12})$-alkyl, particularly of structure Ic, Ic* or Id, preferably in each case with alkyl linear, branched or cyclic —$(C_1$-$C_6)$-alkyl,
(iv) where $R^2$, $R^4$, $R^7$, $R^9$ are in each case methyl, ethyl, tert-butyl, isopentyl and $R^3$, $R^5$, $R^6$, $R^9$ are in each case —H, wherein in the alternatives (i), (ii), (iii) and (iv), $R^1$ is preferably in each case independently selected from: —Cl and —Br, preferably chlorine.

The invention also provides a method for preparing a heterocyclic selenophosphite of the general structure I and also the heterocyclic selenophosphites and mixtures selected from the structures I, Ia, Ia*, Ib, Ic, Ic* and Id obtainable by a method of the invention,

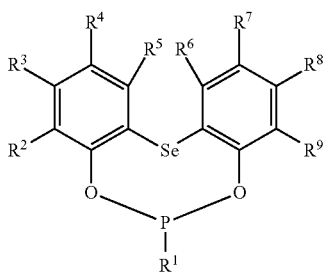
(I)

where $R^2$, $R^3$, $R^4$, $R^5$, $R^6$, $R^7$, $R^8$ and $R^9$ in structure I may each be independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, wherein the alkyl and aryl groups may each be independently unsubstituted or substituted, wherein the respective substituted —$(C_1$-$C_{12})$-alkyl group and substituted —$(C_6$-$C_{20})$-aryl group may have at least one substituent and the at least one substituent may each be independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl and, in particular, the residues $R^2$ to $R^9$ correspond to the residues of structure II, where —$R^1$ is independently selected from —OH and -Hal, where -Hal is selected from fluorine, chlorine, bromine, iodine, particularly preferably chlorine and bromine, particularly preferably chlorine, comprising at least the method step of (i) reacting a selenodiaryl of the general structure II

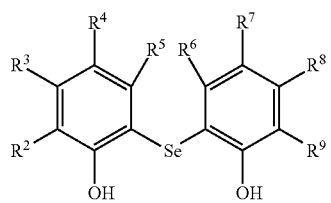
(II)

where $R^2$, $R^3$, $R^4$, $R^5$, $R^6$, $R^7$, $R^8$ and $R^9$ in structure II may each be independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, wherein
the alkyl and aryl groups may each be independently unsubstituted or substituted.
wherein the respective substituted —$(C_1$-$C_{12})$-alkyl group and substituted —$(C_6$-$C_{20})$-aryl group may have at least one substituent and the at least one substituent may each be independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, (ii) with P(Hal)$_3$ of formula III, where -Hal is selected from fluorine, chlorine, bromine, iodine, particularly preferably chlorine and bromine, particularly preferably chlorine, preferably reacting with P(Hal)$_3$ of the formula III comprising PCl$_3$ or PBr$_3$, particularly preferably PCl$_3$ (iii) and obtaining at least one heterocyclic selenophosphite of the general structure I, optionally in a mixture with a rearrangement product of the selenophosphite of the general structure I.

Furthermore, the invention provides a method in which the heterocyclic selenophosphite of the general structure I is obtained as a compound of structure Ia, as shown above, in a mixture with a compound of structure Ia*.

The reaction in the method is carried out in the presence of a base, particularly an amine or a pyridine base, in particular an alkylamine such as triethylamine or dimethylaminobutane, particularly triethylamine.

Furthermore, the reaction is carried out preferably by reacting the selenodiaryl of the general structure II, as disclosed above, with P(Hal)$_3$ of the formula III in a molar ratio of from 10:1 to 1:10, preferably in a ratio of from 1.2:1 to 1:1.2. It is furthermore preferred in this case if the reaction is carried out preferably in a temperature range of −45 to 80° C., especially −15 to 30° C., particularly −5 to 25° C.

By choice of the solvent used in the method, the formation of the method products can be steered towards the formation of the halogenated heterocyclic selenophosphite of structure Ib or Id or alternatively towards the formation of the hydroxy-functional heterocyclic selenophosphites Ia and Ia*, Ic and Ic*. By using anhydrous organic aromatic hydrocarbons such as toluene, xylene etc., the halogenated heterocyclic selenophosphite is obtained whereas using aprotic, anhydrous solvents such as ethers, THF, the hydroxy-functional heterocyclic selenophosphites are predominantly obtained.

According to an alternative, the invention provides a method in which the reaction is carried out in an aprotic solvent, in particular, the solvent in an alternative method is selected from a) organic aromatic halogenated solvents or hydrocarbons and in a second alternative b) from ethers such as diethyl ether, THF, esters, ketones.

According to a further embodiment, the invention relates to the use of at least one heterocyclic selenophosphite of the aforementioned structures I, Ia, Ia*, Ib, Ic, Ic* and Id or the compositions obtainable by the method according to the invention for preparing ligands, particularly as ligand unit for preparing phosphite ligands. Particular preference is given to the selenophosphite ligand units of structure Ia, Ib, Ic and Id and thus intermediates for preparing ligands such as phosphite ligands.

One or more substituents in the aforementioned structures of the selenophosphites and selenodiaryls comprise preferably 1 to 10 substituents, in particular 1 to 3.

In the context of the invention, the expression "—$(C_1$-$C_{12})$-alkyl" encompasses straight-chain and branched alkyl groups. Preferably, these groups are unsubstituted straight-chain or branched —$(C_1$-$C_8)$-alkyl groups and most preferably —$(C_1$-$C_6)$-alkyl groups. Examples of —$(C_1$-$C_{12})$-alkyl groups are particularly methyl, ethyl, propyl, Isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

Halogen includes fluorine, chlorine, bromine and iodine, wherein particular preference is given to chlorine and fluorine.

All elucidations relating to the expression —$(C_1$-$C_{12})$-alkyl in the aforementioned structures of the selenophosphites and selenodiaryls according to the invention also apply to the alkyl groups in —O—$(C_1$-$C_{12})$-alkyl, that is, in —$(C_1$-$C_{12})$-alkoxy.

Preference is given to unsubstituted straight-chain or branched —$(C_1$-$C_6)$-alkoxy groups.

Substituted —$(C_1$-$C_{12})$-alkyl groups and substituted —$(C_1$-$C_{12})$-alkoxy groups in the aforementioned structures of the selenophosphites and selenodiaryls may have one or more substituents, depending on their chain length. The substituents are preferably each independently selected from: —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl. This definition applies to all substituted alkyl or alkoxy groups of the present invention.

All elucidations relating to the expression —$(C_6$-$C_{20})$-aryl in the aforementioned structures of the selenophosphites and selenodiaryls according to the invention also apply to the aryl groups in —O—$(C_6$-$C_{20})$-aryl.

Preference is given to unsubstituted —O—$(C_6$-$C_{20})$— groups.

In the context of the present invention, the expression "—$(C_6$-$C_{20})$-aryl and —$(C_6$-$C_{20})$-aryl-$(C_6$-$C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6$-$C_{10})$-aryl and —$(C_6$-$C_{10})$-aryl-$(C_6$-$C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

The expression "—$(C_3$-$C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl or adamantyl.

One example of a substituted cycloalkyl would be menthyl.

The expression "—$(C_3$-$C_{12})$-heterocycloalkyl groups", in the context of the present invention, encompasses nonaromatic, saturated or partly unsaturated cycloaliphatic groups having 3 to 12, especially 5 to 12, carbon atoms. The —$(C_3$-$C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— or —S(=O)—. Examples of —$(C_3$-$C_{12})$-heterocycloalkyl groups are tetrahydrothiophenyl, tetrahydrofuryl, tetrahydropyranyl and dioxanyl.

The invention is further illustrated in detail below by examples without the invention being limited to the working examples.

GENERAL METHODS

Solvents and Reagents

All reactions with moisture- and/or oxygen-sensitive substances were carried out in baked-out apparatuses under an argon atmosphere. Solvents for extraction and column chromatography were used at the following purities: dichloromethane (99.9%, Walter, Cat. No. BIE 073107033) ethyl acetate (99.5%, Walter, Cat. No. BIE 003917025) and n-hexane (95%, Walter (Baker). Cat. No. 8669), n-heptane (95%, Walter (Baker). Cat. No. 8662). Other solvents for extraction and column chromatography were of technical quality and were used without further purification unless otherwise stated. Dry solvents (abs.) were purified using a Pure Solv MD-7 System and stored under an argon atmosphere. Benzyl bromide was freshly distilled (17 mbar/82° C.) prior to use. Deuterated solvents were distilled from the drying agents specified: dichloromethane-$d_2$ (phosphorus pentoxide), toluene-ds (1. KOH; 2, sodium). Chemicals used for the syntheses were supplied by Sigma Aldrich, Alfa Aesar. Acros Organics, Avantor Performance Materials B. V., Merck KGaA and ABCR GmbH & Co. KG. These were used without further purification unless otherwise stated.

Filtration: Filtrations for the removal of resulting solids were carried out using a G4 frit (pore width: 10-16 μm).

Analysis

IR spectroscopy: IR spectra were recorded with a Nicolet 6700 FT-IR spectrometer from Thermo Electron. The substances were measured by ATR methods.

$^1$H-NMR spectroscopy. $^1$H-NMR spectra were recorded with a model AV300 (300 MHz) and with the model Fourier 300 (300 MHz) from Bruker. Chemical shifts are stated in units on the δ-scale. The residual proton signals of the solvent (dichloromethane-$d_2$: δ=5.32 ppm, toluene-ds: δ=7.09; 7.00; 6.98; 2.09 ppm) served as standard.

$^1$H-NMR spectroscopy: $^{13}$C-NMR spectra were recorded with models AV 300 (75 MHz) and Fourier 300 (75 MHz) from Bruker. The signal of the solvent (dichloromethane-$d_2$: δ=54.0 ppm, toluene-$d_6$: δ=137.9; 129.2; 128.3; 125.5; 20.4 ppm) served as internal standard wherein the chemical shifts were taken from the broadband $^1$H-decoupled spectra.

$^{77}$Se-NMR spectroscopy: $^{77}$Se-NMR spectra were recorded with an AV 300 (57 MHz) from Bruker. The spectra were measured in broadband $^1$H-decoupled mode. The chemical shifts are reported in ppm.

Mass spectrometry: EI mass spectra were recorded on a Finnigan MAT 95-XP instrument from Thermo Electron and ESI-TOF mass spectra with a model 6210 Time-of-Flight LC/MS from Agilent.

X-Ray Crystal Structure Analysis of the Compound of Structure Id (2c)

Data were collected by a Bruker Kappa APEX II Duo diffractometer. The structure was solved by direct methods (SHELXS-97: G. M. Sheldrick, *Acta Cryst*, 2008, A64, 112-122.) and refined with full matrix by the method of least squares against $F^2$ (SHELXL-2014: G. M. Sheldrick, *Acta Cryst* 2015, C71, 3-8.)

General Procedure 8.2 mmol of the particular phenol are dissolved in the appropriate solvent (8.2 m). The reaction mixture is heated, and 4.9 mmol of selenium dioxide are added while stirring. The solvent is distilled under reduced pressure (temperature <70° C.). A frit is prepared with 2.5 cm of silica gel (at the bottom) and 2.5 cm of zeolite (at the top). The distillation residue is taken up in the eluent and applied to the filtration column. Cyclohexane:ethyl acetate (95:5) is used to wash the product off the frit and collect it in fractions. The fractions containing the product are combined and freed of the eluent by distillation. The fractions obtained are recrystallized from 95:5 cyclohexane:ethyl acetate. For this purpose, the solid residue is dissolved at 50° C., and insoluble residues are filtered off using a glass frit. The selenodiaryl (II) reaction product crystallizes out of the saturated solution at room temperature overnight. The resulting crystals are washed once again with cold cyclohexane.

The structural formula shows the main product of the general structure II obtained in each reaction.

Bis(3,5-dimethyl-2-hydroxyphenyl)selenium (II)

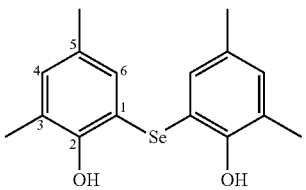

The reaction is conducted according to the general procedure in a screw-top test tube. For this purpose, 1.00 g (8.2 mmol, 1.0 equiv.) of 2,4-dimethylphenol and 0.54 g (4.9 mmol, 0.6 equiv.) of selenium dioxide are dissolved in 1 mL of pyridine and heated. The product is obtained as a colourless crystalline solid.

$^1$H-NMR (400 MHz, CDCl$_3$): δ (ppm)=7.12 (s, 2H, 6-H), 6.91 (s, 2H, 4-H), 5.97 (s, 2H. OH), 2.23 (s, 6H, 3-CH$_3$) 2.23 (s, 6H, 5-CH$_3$); $^{13}$C-NMR (100 MHz, CDCl$_3$): δ (ppm)=151.7 (C-2), 133.2 (C-3), 133.1 (C-5), 130.4 (C-4), 124.2 (C-6), 114.9 (C-1), 20.3 (5-CH$_3$), 16.5 (3-CH$_3$). $^{77}$Se-NMR (76 MHz, CDCl$_3$): δ (ppm)=163.36 ppm.

Bis(3-tert-butyl-5-methyl-2-hydroxyphenyl)selenium (II)

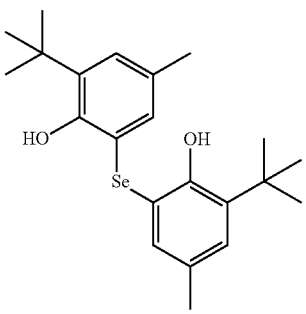 [SMILES: Cc1cc([Se]c2cc(C)cc(C(C)(C)C)c2O)c(O)c(C(C)(C)C)c1]

The reaction is conducted according to the general procedure in a screw-top test tube. Here 1.32 g (8.0 mmol, 1.0 equiv.) of 2-tert-butyl-4-methylphenol and 0.54 g (4.9 mmol, 0.6 equiv.) of selenium dioxide are dissolved in 1 mL of pyridine and heated.

$^1$H-NMR (300 MHz, CDCl$_3$): δ (ppm)=7.15 (s, 2H, 6-H), 7.05 (s, 2H, 4-H), 5.07 (s, 2H, OH), 2.21 (s, 6H, 5-CH$_3$), 2.21 (s, 18H, 3-C(CH$_3$)$_3$; $^{13}$C-NMR (75 MHz, CDCl$_3$):
δ (ppm)=152.1, 136.4, 133.4, 120.1, 129.5, 117.2, 35.1, 29.6, 20.8.

3,3'5,5-Tetra-tert-butylbiphenyl-2,2'-diol (II)

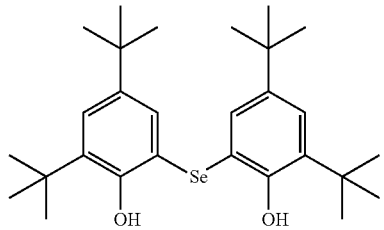 [SMILES: CC(C)(C)c1cc([Se]c2cc(C(C)(C)C)cc(C(C)(C)C)c2O)c(O)c(C(C)(C)C)c1]

The reaction is conducted according to the general procedure in a screw-top test tube. Here 1.67 g (8.2 mmol, 1.0 equiv.)
of 2,4-di-tert-butylphenol and 0.55 g (4.9 mmol, 0.6 equiv.) of selenium dioxide are dissolved in 1 mL of pyridine and heated.

$^1$H-NMR (400 MHz, CDCl$_3$): δ (ppm)=7.31 (d, J=2.4 Hz, 2H), 7.29 (d, J=2.4), 6.29 (s, 2H), 1.42 (s, 18H), 1.24 (s, 18H); $^{13}$C-NMR (75 MHz, CDCl$_3$): δ (ppm)=151.7, 143.5, 135.8, 129.8, 125.6, 117.2, 35.4, 34.4, 31.6, 29.7.

Preparation of a Seleno-Heterocyclic Monophosphite of Structure I

Synthesis of 2,4,8,10-Tetramethyldibenzo[d,g][1,3, 6,2]dioxaselenophosphocin-6-ol Ic (2a) and 2,4,8, 10-tetramethyldibenzo[d,g][1,3,6,2]dioxaselenophosphocin-6-oxide Ic* (2b) and 6-choloro-2,4,6, 10-tetramethyldibenzo[d,g][1,3,6,2] dioxaselenophosphocin Id (2c)

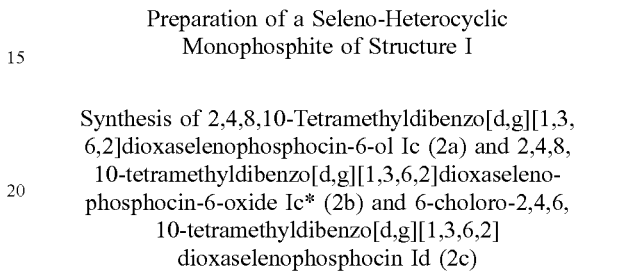

In a baked-out, 50 mL Schlenk flask under an argon atmosphere, 87.5 μL (137 mg, 1.00 mmol, 1.0 eq) of phosphorus trichloride and 322 mg (1.00 mmol, 1.0 eq) of selenodiphenol 1 were dissolved in 15 mL of abs, diethyl ether. The pale yellow solution was cooled to 0° C. and a solution of 277 μL (202 mg, 2.00 mmol, 2.0 eq) of triethylamine in 2.5 mL of abs, diethyl ether was added dropwise, whereupon the formation of a colourless precipitate was observed. 4.0 mL of abs, diethyl ether were rinsed in and the mixture stirred for 10 minutes at 0° C. The reaction solution was subsequently heated to RT and stirred for a further 36 hours. The resulting precipitate was filtered off and the solid washed with 5.0 mL of abs, diethyl ether. The solvent was removed under reduced pressure and the crude product was dried under vacuum at 50° C. for three hours. 386 mg (0.999 mmol, 99%) of the title compounds 2a and 2b were obtained as a colourless solid in a ratio of 85:15 (determined by $^{31}$P-NMR).

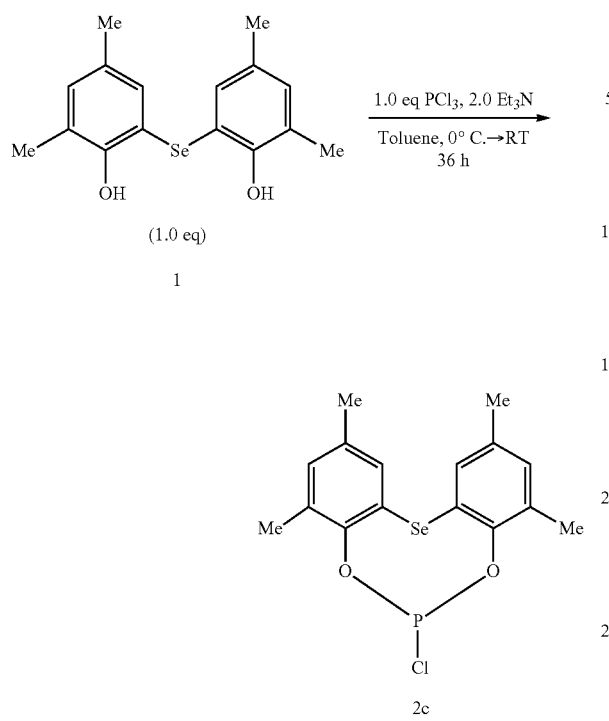

If the reaction was carried out in abs, toluene in place of abs, diethyl ether (analogous experimental procedure), 6-chloro-2,4,8,10-tetramethyldibenzo[d,g][1,3,6,2]dioxaseleno phosphocin Id (2c) was obtained. The compound is crystalline and from the crystals of compound 2c obtained, a single crystal structure analysis could be performed.

Total reaction mixture: IR (ATR): $\tilde{\nu}$ (cm$^{-1}$)=3205; 2916; 2853; 2730; 2465; 1460; 1423; 1376; 1272; 1191; 1115; 1037; 957; 934; 917; 887; 859; 812; 733; 671; 594; 579; 567; 526; 497; 475.

Total reaction mixture: $^{77}$Se-NMR (57 MHz, toluene-d$_8$): δ (ppm)=313.5 ppm (d, $J_{Se-P}$=59.7 Hz); 319.3 ppm (d, J=4.38 Hz); 326.0 ppm (d, $J_{Se-P}$=50.9 Hz).

Compounds 2a/2b: $^{31}$P-NMR (122 MHz, toluene-d$_6$): δ (ppm)=167.0 ($J_{P-Se}$=59.5 Hz); −2.45.

Compounds 2a/2b: $^1$H-coupled $^{31}$P-NMR (122 MHz, toluene-d$_8$): δ (ppm)=167.0 ($J_{P-Se}$=59.5 Hz); −2.41 (d, $J_{P-H}$=745 Hz).

Total reaction mixture: $^{31}$P-NMR (122 MHz, toluene-d): δ (ppm)=197.9 (d, J=12.4 Hz); 167.0; 136.5; 136.0 (d, J=12.4 Hz), −2.45.

Compounds 2a/2b: ESI-TOF/MS: m/z=369.016 ([M+H]$^+$); 390.998 ([M+Na]$^+$); 759.006 ([2M+Na]).

For compounds 2a/2b: HR-MS (ESI-TOF): calc. for C$_{16}$H$_{18}$O$_3$PSe ([M+H]$^+$): 369.0154. found: 369.0157; calc. for C$_{16}$H$_{17}$O$_3$PSeNa ([M+Na]$^+$): 390.99734. found: 390.99808.

For compounds 2a/2b: C$_{16}$H$_{17}$O$_3$PSe (368.01 g/mol).

For compound 2c: C$_{16}$H$_{16}$ClO$_2$PSe (385.97 g/mol).

Theoretical calculation of compounds 2a/2b:

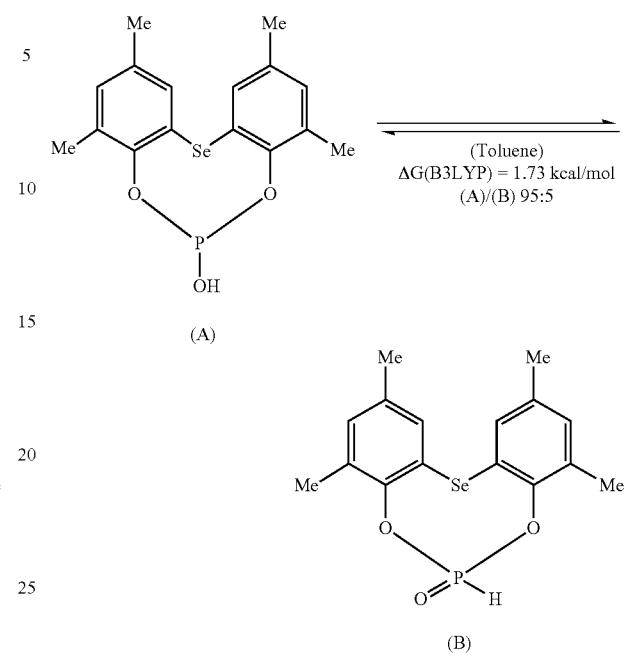

Crystal structure analysis of the compound of structure Id (2c):

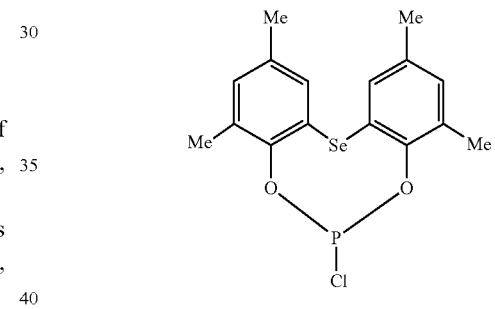

Compound 2c: C$_{16}$H$_{16}$ClO$_2$PSe, M=385.67, monoclinic, space group P2$_1$/c, a=11.9587 (5), b=8.8151 (4), c=15.6401 (7) Å, β=93.4819 (16)°, V=1645.69 (13) Å$^3$, Z=4, ρ$_{cal.}$=1.557 g·cm$^{-3}$, μ=2.542 mm$^{-1}$, T=150 (2) K, 26607 measured, 3977 independent reflections (R$_{int}$=0.0215), R$_1$=0.0245 (I>2σ (1)), wR$_2$=0.0691 (all data), 194 parameters. Measurable crystals of compound 2c could be obtained in a solvent mixture of n-heptane/acetonitrile (5:1) at a temperature of 6° C. (refrigerator).

The invention claimed is:

1. A compound of a heterocyclic selenophosphite having a general structure (I)

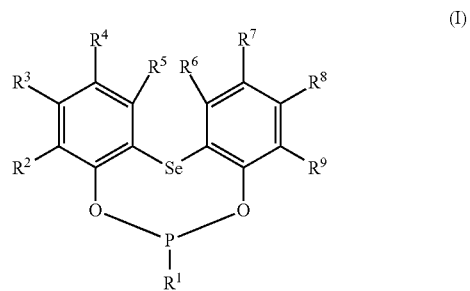

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_6$-$C_{20}$)-aryl, —COOH, —SO$_3$H, —CN, or —[($C_1$-$C_{12}$)-alkyl]$_2$, wherein the alkyl and aryl groups are each independently unsubstituted or substituted, wherein the respective substituted —($C_1$-$C_{12}$)-alkyl group and substituted —($C_6$-$C_{20}$)-aryl group has at least one substituent and the at least one substituent is each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and where —$R^1$ is independently selected from —OH and -Hal, and -Hal is selected from fluorine, chlorine, bromine, or iodine, and wherein optionally the compound of structure (I) is present in a mixture with a rearrangement product of structure (I).

2. The compound according to claim 1, wherein the heterocyclic selenophosphite of the general structure (I) is present as a compound of structure (Ia) in a mixture with a compound of structure (Ia*),

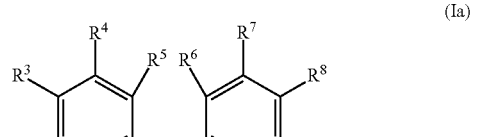
(Ia)

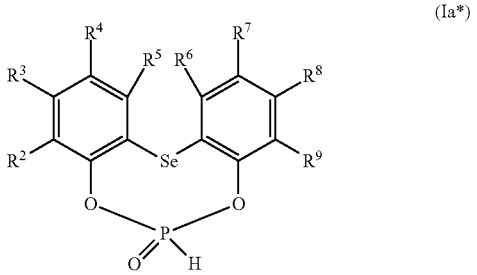
(Ia*)

where $R^2$, $R^3$, $R^4$, $R^5$, $R^6$, $R^7$, $R^8$ and $R^9$ in structures (Ia) and (Ia*) are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —SO$_3$H, —CN, or —N[($C_1$-$C_{12}$)-alkyl]$_2$, wherein the alkyl and aryl groups are each independently unsubstituted or substituted, wherein the respective substituted —($C_1$-$C_{12}$)-alkyl group and substituted —($C_6$-$C_{20}$)-aryl group has at least one substituent and the at least one substituent is each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl.

3. The compound according to claim 1, wherein the heterocyclic selenophosphite of the general structure (I) is a compound of structure (Ib),

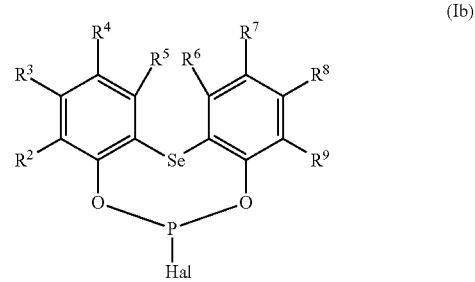
(Ib)

where $R^2$, $R^3$, $R^4$, $R^5$, $R^6$, $R^7$, $R^8$ and $R^9$ in structure (Ib) are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —SO$_3$H, —CN, or —N[($C_1$-$C_{12}$)-alkyl]$_2$, wherein the alkyl and aryl groups are each independently unsubstituted or substituted, wherein the respective substituted —($C_1$-$C_{12}$)-alkyl group and substituted —($C_6$-$C_{20}$)-aryl group has at least one substituent and the at least one substituent is each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and wherein -Hal is selected from fluorine, chlorine, bromine, or iodine.

4. The compound according to claim 1, wherein the heterocyclic selenophosphite of the general structure (I) is a compound of structure (Ic) or (Ic*), wherein optionally the compounds of structures (Ic) and (Ic*) are present as a mixture

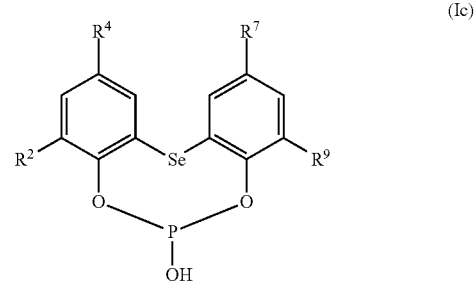
(Ic)

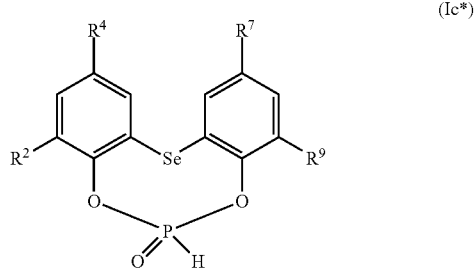
(Ic*)

where $R^2$, $R^4$, $R^7$, and $R^9$ in structures (Ic) and (Ic*) are each independently selected from: —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —SO$_3$H, —CN, or —N[($C_1$-$C_{12}$)-alkyl]$_2$, wherein the alkyl and aryl groups are each independently unsubstituted or substituted, wherein the respective substituted —(C$_1$-C$_{12}$)-alkyl group and substituted —(C$_6$-C$_{20}$)-aryl group has at least one substituent and the at least one substituent is each independently selected from —(C$_3$-C$_{12}$)-cycloalkyl, —(C$_3$C$_{12}$)-heterocycloalkyl, —(C$_6$-C$_{20}$)-aryl, fluorine, chlorine, cyano, formyl, acyl or alkoxycarbonyl.

5. The compound according to claim 1, wherein
the heterocyclic selenophosphite of the general structure (I) is a compound of structure (Id),

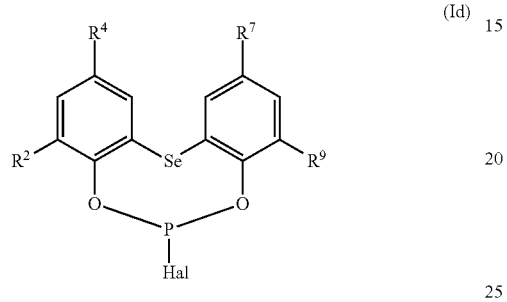

where R$^2$, R$^4$, R$^7$ and R$^9$ in structure (Id) are each independently selected from: —(C$_1$-C$_{12}$)-alkyl, —O—(C$_1$-C$_2$)-alkyl, —(C$_6$-C$_{20}$)-aryl, —O—(C$_6$-C$_{20}$)-aryl, -halogen, —COO—(C$_1$-C$_{12}$)-alkyl, —CONH—(C$_1$-C$_{12}$)-alkyl, —CO—(C$_1$-C$_{12}$)-alkyl, —CO—(C$_6$-C$_{20}$)-aryl, —COOH, —SO$_3$H, —CN, or —N[(C$_1$-C$_{12}$)-alkyl]$_2$, wherein the alkyl and aryl groups are each independently unsubstituted or substituted, wherein the respective substituted —(C$_1$-C$_{12}$)-alkyl group and substituted —(C$_6$-C$_{20}$)-aryl group has at least one substituent and the at least one substituent is each independently selected from —(C$_3$-C$_{12}$)-cycloalkyl, —(C$_3$-C$_{12}$)-heterocycloalkyl, —(C$_6$-C$_{20}$)-aryl, fluorine, chlorine, cyano, formyl, acyl or alkoxycarbonyl, where -Hal is selected from fluorine, chlorine, bromine, or iodine.

6. A method for preparing at least one heterocyclic selenophosphite of the general structure (I)

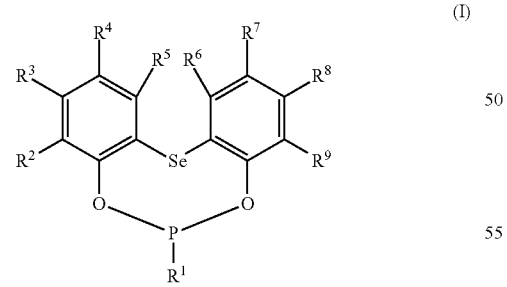

where R$^2$, R$^3$, R$^4$, R$^5$, R$^6$, R$^7$, R$^8$ and R$^9$ are each independently selected from: —H, —(C$_1$-C$_{12}$)-alkyl, —O—(C$_1$-C$_{12}$)-alkyl, —(C$_6$-C$_{20}$)-aryl, —O—(C$_6$-C$_{20}$)-aryl, -halogen, —COO—(C$_1$-C$_{12}$)-alkyl, —CONH—(C$_1$-C$_{12}$)-alkyl, —CO—(C$_1$-C$_{12}$)-alkyl, —CO—(C$_6$-C$_{20}$)-aryl, —COOH, —SO$_3$H, —CN, or —N[(C$_1$-C$_{12}$)-alkyl]$_2$, wherein the alkyl and aryl groups are each independently unsubstituted or substituted, wherein the respective substituted —(C$_1$-C$_{12}$)-alkyl group and substituted —(C$_6$-C$_{20}$)-aryl group has at least one substituent and the at least one substituent is each independently selected from —(C$_3$-C$_{12}$)-cycloalkyl, —(C$_3$-C$_{12}$)-heterocycloalkyl, —(C$_6$-C$_{20}$)-aryl, fluorine, chlorine, cyano, formyl, acyl or alkoxycarbonyl, and where —R$^1$ is independently selected from —OH and -Hal, where -Hal is selected from fluorine, chlorine, bromine, or iodine, optionally in a mixture with a rearrangement product of the compound of the structure (I), comprising at least the method step of (i) reacting a selenodiaryl of the general structure (II)

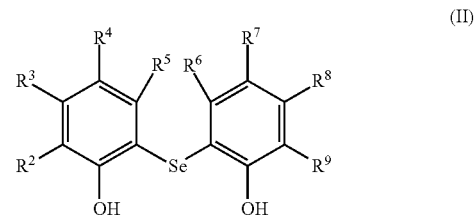

where R$^2$, R$^3$, R$^4$, R$^5$, R$^6$, R$^7$, R$^8$ and R$^9$ in structure (II) are each independently selected from: —H, —(C$_1$-C$_{12}$)-alkyl, —O—(C$_1$-C$_{12}$)-alkyl, —(C$_6$-C$_{20}$)-aryl, —O—(C$_6$-C$_{20}$)-aryl, -halogen, —COO—(C$_1$-C$_{12}$)-alkyl, —CONH—(C$_1$-C$_{12}$)-alkyl, —CO—(C$_1$-C$_{12}$)-alkyl, —CO—(C$_6$-C$_{20}$)-aryl, —COOH, —SO$_3$H, —CN, or —N[(C$_1$-C$_{12}$)-alkyl]$_2$, wherein the alkyl and aryl groups are each independently unsubstituted or substituted, wherein the respective substituted —(C$_1$-C$_{12}$)-alkyl group and substituted —(C$_6$-C$_{20}$)-aryl group has at least one substituent and the at least one substituent is each independently selected from —(C$_3$-C$_{12}$)-cycloalkyl, —(C$_3$-C$_{12}$)-heterocycloalkyl, —(C$_6$-C$_{20}$)-aryl, fluorine, chlorine, cyano, formyl, acyl or alkoxycarbonyl, (ii) with P(Hal)$_3$, where -Hal is selected from fluorine, chlorine, bromine, or iodine, (iii) and obtaining at least one heterocyclic selenophosphite of the general structure (I), optionally in a mixture with a rearrangement product of the compound of the structure (I).

7. The method according to claim 6, wherein
the heterocyclic selenophosphite of the general structure (I) is a compound of structure (Ia) in a mixture with a compound of structure (Ia*),

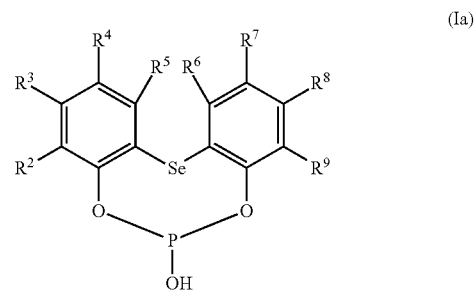

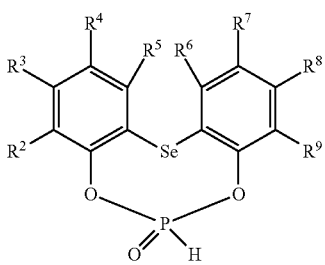

where $R^2$, $R^3$, $R^4$, $R^5$, $R^6$, $R^7$, $R^8$ and $R^9$ in structure (Ia) and (Ia*) are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, or —N[($C_1$-$C_{12}$)-alkyl]$_2$, wherein the alkyl and aryl groups are each independently unsubstituted or substituted, wherein the respective substituted —($C_1$-$C_{12}$)-alkyl group and substituted —($C_6$-$C_{20}$)-aryl group has at least one substituent and the at least one substituent is each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl.

8. The method according to claim 6, wherein (i) the reaction is carried out in the presence of an amine.

9. The method according to claim 6, wherein the selenodiaryl of the general structure (II) is reacted with P(Hal)$_3$ in a molar ratio of from 10:1 to 1:10.

10. The method according to claim 6, wherein P(Hal)$_3$ is PCl$_3$ or PBr$_3$.

11. The method according to claim 6, wherein (i) the reaction is carried out from −15 to 30° C.

12. The method according to claim 6, wherein (i) the reaction is carried out in an aprotic solvent.

13. The method of claim 8, wherein (i) the reaction is carried out in the presence of an alkylamine.

14. The method of claim 13, wherein the alkylamine is triethylamine.

15. The method of claim 9, wherein the selenodiaryl of the general structure (II) is reacted with P(Hal)$_3$ in a molar ratio of from 1.2:1 to 1:1.2.

16. The method of claim 11, wherein (i) the reaction is carried out from −5 to 5° C.

17. The method of claim 12, wherein the aprotic solvent is selected from a) organic aromatic halogenated solvents or hydrocarbons, or b) ethers, THF, esters or ketones.

* * * * *